United States Patent
Bhattacharyya et al.

(10) Patent No.: US 8,946,471 B2
(45) Date of Patent: Feb. 3, 2015

(54) PROCESS FOR OXIDIZING AN ALKYL-AROMATIC COMPOUND

(75) Inventors: Alakananda Bhattacharyya, Des Plaines, IL (US); Joel T. Walenga, Des Plaines, IL (US)

(73) Assignee: UOP LLC, Des Plaines, IL (US)

(*) Notice: Subject to any disclaimer, the term of this patent is extended or adjusted under 35 U.S.C. 154(b) by 253 days.

(21) Appl. No.: 13/340,152

(22) Filed: Dec. 29, 2011

(65) Prior Publication Data

US 2013/0172608 A1 Jul. 4, 2013

(51) Int. Cl.
C07C 51/265 (2006.01)

(52) U.S. Cl.
USPC .......................... 562/412; 562/416

(58) Field of Classification Search
USPC .................. 562/412, 416
See application file for complete search history.

(56) References Cited

U.S. PATENT DOCUMENTS

| | | | |
|---|---|---|---|
| 7,485,747 B2* | 2/2009 | Sheppard et al. | 562/487 |
| 7,985,875 B2* | 7/2011 | Hashmi et al. | 562/416 |
| 2004/0015009 A1 | 1/2004 | Earle | |
| 2007/0208193 A1* | 9/2007 | Wonders et al. | 562/410 |
| 2008/0191170 A1 | 8/2008 | Walker et al. | |
| 2009/0270248 A1 | 10/2009 | Earl et al. | |
| 2009/0326265 A1 | 12/2009 | Hashmi | |
| 2010/0174111 A1 | 7/2010 | Rogers | |

FOREIGN PATENT DOCUMENTS

WO WO 2010/122304 10/2010

OTHER PUBLICATIONS

International Search Report for PCT/US2012/059183, dated Jan. 17, 2013.

* cited by examiner

*Primary Examiner* — Kamal Saeed
*Assistant Examiner* — Janet L Coppins (57) ABSTRACT

Processes for oxidizing an alkyl-aromatic compound are described. The processes include contacting an alkyl-aromatic compound, a solvent, a bromine source, a catalyst, and an oxidizing agent to produce a product comprising at least one of an aromatic alcohol, an aromatic aldehyde, an aromatic ketone, and an aromatic carboxylic acid. The composition of the solvent is controlled to reduce the impurities in the product.

20 Claims, 2 Drawing Sheets

PROCESS FOR OXIDIZING AN ALKYL-AROMATIC COMPOUND

FIELD OF THE INVENTION

This invention relates to processes for oxidizing alkyl-aromatic compound. More particularly, the invention relates to processes for reducing the impurities and/or improving the color of the oxidized alkyl-aromatic compounds.

BACKGROUND OF THE INVENTION

Oxidation of alkyl aromatic compounds, e.g., toluene and xylenes are important commercial processes. A variety of oxidation products may be obtained including aromatic carboxylic acids such as terephthalic acid (1,4-benzenedicarboxylic acid) and isophthalic acid (1,3-benzenedicarboxylic acid) which are used, for example, in the polymer industry.

It is known that oxidation products, such as aromatic alcohols, aromatic aldehydes, aromatic ketones, and aromatic carboxylic acids, may solidify or crystallize at oxidation conditions and/or as the reaction mixture cools. Thus, mixtures of oxidation products may be produced which require further processing to increase the purity of the desired product. For example, in the production of terephthalic acid, the oxidation product is often referred to as crude terephthalic acid because it contains impurities including color bodies and intermediate oxidation products, especially 4-carboxybenzaldehyde (4-CBA). To obtain polymer grade or purified terephthalic acid, various purification steps are known in the art including: washing the crude terephthalic acid with water and/or a solvent, additional oxidation or crystallization steps, and reacting a solution of dissolved crude terephthalic acid with hydrogen at hydrogenation conditions usually including a catalyst comprising palladium and carbon. Often several purification steps are used.

U.S. Pat. No. 2,833,816 discloses processes for oxidizing aromatic compounds to the corresponding aromatic carboxylic acids. A process for the liquid phase oxidation of alkyl aromatic compounds uses molecular oxygen, a metal or metal ions, and bromine or bromide ions in the presence of an acid. The metals may include cobalt and/or manganese. Exemplary acids are lower aliphatic mono carboxylic acids containing 1 to 8 carbon atoms, especially acetic acid.

U.S. Pat. No. 6,355,835 discloses a process for the preparation of benzene dicarboxylic acids by liquid phase oxidation of xylene isomers using oxygen or air by oxidizing in the presence of acetic acid as a solvent, a cobalt salt as a catalyst, and an initiator. The oxidation step is followed by flashing the reaction mixture to remove volatile substances and cooling and filtering the material to get crude benzene di-carboxylic acid as a solid product and a filtrate. Recrystallizing the crude benzene di-carboxylic acid to obtain at least 99% purity and recycling of the filtrate are also disclosed.

U.S. Pat. No. 7,094,925 discloses a process for preparing an alkyl-aromatic compound. The process includes mixing an oxidizing agent or sulfur compound in the presence of an ionic liquid. Air, dioxygen, peroxide, superoxide, or any other form of active oxygen, nitrite, nitrate, and nitric acid or other oxides or oxyhalides of nitrogen (hydrate or anhydrous) can be used as the oxidizing agent. The process is typically carried out under Bronstead acidic conditions. The oxidation is preferably performed in an ionic liquid containing an acid promoter, such as methanesulfonic acid. The product is preferably a carboxylic acid or ketone or intermediate compound in the oxidation, such as an aldehyde, or alcohol.

U.S. Pat. No. 7,985,875 describes a process for preparing an aromatic polycarboxylic acid by liquid phase oxidation of a di- or tri-substituted benzene or naphthalene compound. The process involves contacting the aromatic compound with an oxidant in the presence of a carboxylic acid solvent, a metal catalyst, and a promoter in a reaction zone. The promoter is an ionic liquid comprising an organic cation and a bromide or iodide anion. The promoter is used in a concentration range of about 10 to about 50,000 ppm (based on solvent) with a preferred range of 10-1,000 ppm. No other promoters, such as bromine-containing compounds, need to be used in the process. The process produces crude terephthalic acid (CTA) having 1.4-2.2% 4-CBA. Purification of the CTA is required to obtain purified terephthalic acid (PTA).

US 2010/0174111 describes a process for purifying aryl carboxylic acids, such as terephthalic acid. The impure acid is dissolved or dispersed in an ionic liquid. A non-solvent (defined as a molecular solvent for which the ionic solvent has high solubility and for which the aryl carboxylic acid has little or no solubility) is added to the solution to precipitate the purified acid.

U.S. Pat. Nos. 7,692,036, 2007/0155985, 2007/0208193, and 2010/0200804 disclose a process and apparatus for carrying out the liquid-phase oxidation of an oxidizable compound. The liquid phase oxidation is carried out in a bubble column reactor that provides for a highly efficient reaction at relatively low temperatures. When the oxidized compound is para-xylene, the product from the oxidation reaction is CTA which must be purified. Purification is said to be easier than for conventional high temperature processes.

SUMMARY OF THE INVENTION

One aspect of the invention is a process for oxidizing an alkyl-aromatic compound. In one embodiment, the process includes contacting an alkyl-aromatic compound, a solvent, a bromine source, a catalyst, and an oxidizing agent to produce a product comprising at least one of an aromatic alcohol, an aromatic aldehyde, an aromatic ketone, and an aromatic carboxylic acid; wherein the solvent comprises a carboxylic acid and an ionic liquid and wherein the solvent has a ratio of the carboxylic acid to the ionic liquid within a range of about 7:13 and 13:7 by weight.

In another embodiment, the process includes contacting an alkyl-aromatic compound, a solvent, a bromine source, a catalyst, and an oxidizing agent to produce a product comprising at least one of an aromatic alcohol, an aromatic aldehyde, an aromatic ketone, and an aromatic carboxylic acid; and maintaining a 4-CBA level in the product of less than about 2500 ppm by controlling a ratio of the solvent.

Another embodiment of the process involves contacting an alkyl-aromatic compound, a solvent, a bromine source, a catalyst, and an oxidizing agent to produce a product comprising at least one of an aromatic alcohol, an aromatic aldehyde, an aromatic ketone, and an aromatic carboxylic acid; and maintaining a CIELAB b* value of the product to less than about 5 by controlling a ratio of the solvent.

DETAILED DESCRIPTION OF THE INVENTION

It has been discovered that the invention may be used to produce an oxidation product having different amounts of contaminants relative to those observed in conventional processes. The amount of various contaminants in the oxidation product may be controlled by use of the invention.

The color of the product can be an important consideration for some products, for example for terephthalic acid. CIE L*a*b* (CIELAB) is a standard color identification method that was developed as a device independent model to reference visible colors as specified by the International Commission on Illumination (French Commission Internationale de l'éclairage, abbreviated as CIE). The CIELAB scale consists of three measurements: a* (red-green hue), b* (blue-yellow hue) and L* (black-white luminance). PTA technology uses the b* measurement as a standard measurement of commercial purified terephthalic acid whiteness and sets a specific b* color range for between 0.8 and 1.5.

The CIELAB b* value for the present invention is less than about 5, or less than about 4.5, or less than about 4, or less than about 3.5, or less than about 3, or less than about 2.5, or less than about 2, or less than about 1.5. These values can be obtained for the product from the oxidation process described (one or more oxidation steps) without additional purification by hydrogenation.

It was discovered that for making terephthalic acid, the ratio of carboxylic acid to ionic liquid is generally in the range of about 1:3 to about 3:1, and is desirably about 1:1, and the ratio of 1-butyl-3-methylimidazolium acetate to 1-butyl-3-methylimidazolium bromide is generally in the range of about 4:1 to about 1:4, and is desirably about 0.5 to obtain the whitest products with the lowest level of 4-CBA.

In an embodiment, the solvent has a ratio of the carboxylic acid to the ionic liquid within a range of about 1:16 to 16:1 by weight, or about 1:9 to 9:1 by weight, or about 3:17 to 17:3 by weight, or about 1:4 to 4:1 by weight, or about 1:3 to 3:1 by weight, or about 3:7 to 7:3 by weight, or about 7:13 to 13:7 by weight, or about 2:3 to 3:2 by weight, or about 9:11 to 11:9 by weight, or about 1:1 by weight. In an embodiment, the solvent contains more than 5% by weight ionic liquid, or at least about 6% by weight ionic liquid, or at least about 10% by weight ionic liquid, or at least about 15% by weight ionic liquid, or at least about 20% by weight ionic liquid, or at least about 25% by weight ionic liquid, or at least about 30% by weight ionic liquid, or at least about 35% by weight ionic liquid, or at least about 40% by weight ionic liquid, or at least about 45% by weight ionic liquid. The amount of ionic liquid includes ionic liquid precursors, if present. The optional ionic solid or material capable of forming an ionic salt in solution discussed below, if present, is included in the amount of ionic liquid.

A blend of ionic liquid that has a weight ratio of carboxylic acid:1-butyl-3-methylimidazolium bromide:ammonium acetate:1-butyl-3-methylimidazolium acetate of about 10:1:1:1 to about 1:5:5:5 produces the lowest level of 4-CBA and an acceptable white color, and is desirably about 5:2:2:1.

The product made by the process can contain less than about 2500 ppm 4-CBA, or less than about 2000 ppm 4-CBA, or less than about 1500 ppm 4-CBA, or less than about 1000 ppm 4-CBA, or less than about 750 ppm 4-CBA, or less than about 500 ppm 4-CBA, or less than about 250 ppm 4-CBA, or less than about 100 ppm 4-CBA, or less than about 50 ppm 4-CBA, or less than about 25 ppm 4-CBA.

The contacting step(s) may be practiced in laboratory scale experiments through full scale commercial operations. The process may be operated in batch, continuous, or semi-continuous mode. The contacting step can take place in various ways. The order of addition of the components (e.g. alkyl-aromatic compound, solvent, bromine source, catalyst, and oxidizing agent) is not critical. For example, the components can be added individually, or two or more components may be combined or mixed before being combined or mixed with other components.

Suitable alkyl aromatic compounds or feeds to be oxidized include aromatic compounds comprising at least one benzene ring having at least one alkyl group. Methyl, ethyl, and iso-propyl alkyl groups are preferred alkyl groups, although other alkyl groups can be used if desired. In an embodiment, the alkyl aromatic compound is selected from toluene, para-xylene, ortho-xylene, and meta-xylene. The feed may comprise more than one alkyl aromatic compound. As the oxidation reaction generally proceeds through successive degrees of oxidization, suitable feed compounds also include partially oxidized intermediates relative to the desired oxidized product. For example, in the production of terephthalic acid, the alkyl aromatic feed may comprise para-toluic acid and/or 4-carboxybenzaldehyde (4-CBA).

The solvent comprises at least one ionic liquid. Two or more ionic liquids can be used, if desired.

Generally, ionic liquids are non-aqueous, organic salts composed of ions where the positive ion is charge balanced with a negative ion. These materials have low melting points, often below 100° C., undetectable vapor pressure, and good chemical and thermal stability. The cationic charge of the salt is localized over hetero atoms, and the anions may be any inorganic, organic, or organometallic species.

Most ionic liquids are formed from cations that do not contain acidic protons. The synthesis of ionic liquids can generally be split into two parts: formation of the desired cation, and anion exchange to form the desired product. Quaternization of an amine or phosphine, for example, is the initial step in the synthesis of the cation of an ionic liquid. If it is not possible to form the desired anion directly by the quaternization reaction, a further step is required.

There are estimated to be hundreds of thousands of simple ion combinations to make ionic liquids, and an almost endless ($10^{18}$) number of potential ionic liquid mixtures. This implies that it should be possible to design an ionic liquid with the desired properties to suit a particular application by selecting anions, cations, and mixture concentrations. Ionic liquids can be adjusted or tuned to provide a specific melting point, viscosity, density, hydrophobicity, miscibility, etc. for specific applications. The thermodynamics and reaction kinetics of processes carried out in ionic liquids are different from those in conventional media. This creates new opportunities for catalytic reactions, separations, combined reaction/separation processes, heat transfer agents, hydraulic fluids, paint additives, electrochemistry applications, as well as many others. Ionic liquids do not emit volatile organic compounds (VOCs), providing a basis for clean manufacturing, e.g., "green chemistry."

$R^1$ = methyl, vinyl, allyl
$R^2$ = ethyl, propyl, butyl, isobutyl, propargyl, allyl, crotyl, methallyl
X = Cl, Br The organic cation can comprise a linear, branched, or cyclic heteroalkyl unit, as described in US 2010/0174111.

The term "heteroalkyl" refers to a cation comprising one or more heteroatoms chosen from nitrogen, oxygen, sulfur, boron, arsenic, boron, antimony, aluminum, or phosphorous capable of forming a cation. The heteroatom can be a part of a ring formed with one or more other heteroatoms, for example, pyridinyl, imidazolinyl rings, that can have substituted or unsubstituted linear or branched alkyl units attached thereto. In addition, the cation can be a single heteroatom wherein a sufficient number of substituted or unsubstituted linear or branched alkyl units are attached to the heteroatom such that a cation is formed.

Non-limiting examples of heterocyclic and heteroaryl units that can be alkylated to form cationic units include imidazole, pyrazoles, thiazoles, isothiazoles, azathiozoles, oxothiazoles, oxazines, oxazolines, oxazaboroles, dithiozoles, triazoles, selenozoles, oxaphospholes, pyrroles, boroles, furans, thiphenes, phospholes, pentazoles, indoles, indolines, oxazoles, isothirazoles, tetrazoles, benzofuran, dibenzofurans, benzothiophenes, dibenzothoiphenes, thiadiazoles, pyrdines, pyrimidines, pyrazines, pyridazines, piperazines, piperidines, morpholines, pyrans, annolines, phthalazines, quinazolines, and quinoxalines.

The anionic portion of the ionic liquid can comprise an inorganic, organic, or organometallic moiety, as described in US 2010/0174111. Non-limiting examples of anions include inorganic anions: halogens, (e.g., F, Cl, Br, and I); borides, $BX_4$, wherein X represents halogen, (e.g., $BF_4$, $BCl_4$), and the like; phosphates (V), $PX_6^-$; $PF_6^-$, and the like; arsenate (V), $AsX_6^-$; $AsF_6^-$, and the like; stibate (V) (antimony), $SbX_6^-$; $SbF_6^-$, and the like; $CO_3^{2-}$; $NO_2^{1-}$, $NO_3^{1-}$, $SO_4^{2-}$, $PO_4^{3-}$, $(CF_3)SO_3^{1-}$.

Other non-limiting examples of ionic liquid anions include substituted azolates, that is, five membered heterocyclic aromatic rings that have nitrogen atoms in either positions 1 and 3 (imidazolates); 1, 2, and 3 (1,2,3-triazolates); or 1, 2, 4 (1,2,4-triazolate). Substitutions to the ring occur at positions that are not located in nitrogen positions (these are carbon positions) and include CN (cyano-), $NO_2$ (nitro-), and $NH_2$ (amino) group appended to the heterocyclic azolate core.

Further non-limiting examples of anions include substituted or unsubstituted borides: $B(R)_4$; substituted or unsubstituted sulfates: $(RO)S(=O)_2O$; substituted or unsubstituted acyl units $RCO_2$, for example, acetate $CH_3CO_2$, proprionate, $CH_3CH_2CO_2$, butyrate $CH_3CH_2CH_2CO_2$, and benzylate $C_6H_5CO_2$; substituted or unsubstituted phosphates: $(RO)_2P(=O)O$; substituted or unsubstituted carboxylates: $(RO)C(=O)O$; substituted or unsubstituted azolates wherein the azolate can be substituted on a carbon atom by a unit chosen from cyano, nitro, and amino. R can be an organic, inorganic, or organometallic group. Non-limiting examples of R include hydrogen; substituted or unsubstituted linear branched, and cyclic alkyl; substituted or unsubstituted linear, branched, and cyclic alkoxy; substituted or unsubstituted aryl; substituted or unsubstituted aryloxy; substituted or unsubstituted heterocyclic; substituted or unsubstituted heteroaryl; acyl; silyl; boryl; phosphino; amino; thio; and seleno.

In an embodiment, ionic liquids suitable for use include, but are not limited to, one or more of imidazolium ionic liquids, pyridinium ionic liquids, tetra alkyl ammonium ionic liquids, and phosphonium ionic liquids. More than one ionic liquid may be used. Imidazolium, pyridinium, and ammonium ionic liquids have a cation comprising at least one nitrogen atom. Phosphonium ionic liquids have a cation comprising at least one phosphorus atom. In an embodiment, the ionic liquid comprises a cation selected from alkyl imidazolium, di-alkyl imidazolium, and combinations thereof. In another embodiment, the ionic liquid comprises an anion selected from halides, acetate, carboxylates, and combinations thereof. The ionic liquid may comprise at least one of 1-butyl 3-methyl imidazolium acetate (BMImOAc), 1-butyl 3-methyl imidazolium bromide (BMImBr), 1-hexyl 3-methyl imidazolium acetate, and 1-hexyl 3-methyl imidazolium bromide.

The ionic liquid can be provided, or it can be generated in situ from appropriate precursors, or both. If it is generated in situ, the solvent comprises precursors of one or more ionic liquids. The ionic liquid precursors comprise a cation precursor, such as an alkyl imidazole, alkyl pyridine, alkyl amine, alkyl phosphine, and the like, and an anion precursor, such as alkyl or aryl halides or acetates. In an embodiment, the precursors are methyl imidazole and butyl bromide.

The mode of introducing the ionic liquid precursors may vary depending on the nature of the alkyl aromatics being oxidized and the nature and purity of the product desired. In one mode of addition, the cation precursors and the anion precursors (generally liquids at room temperature and pressure) are mixed with a carboxylic acid (for example, acetic acid) solvent and introduced into the oxidation reactor(s). In another mode of addition, the ionic liquid precursors may be mixed with the alkyl aromatic feed and introduced into the oxidation reactors. In another mode of addition, both cation and anion ionic liquid precursor components may be introduced into the bottom of the reactor without pre-mixing with any other oxidation reactor components such as the feed, carboxylic acid solvent, and catalyst package.

The solvent can also comprise a carboxylic acid. When carboxylic acids are used in the solvent, the amount of carboxylic acid is decreased compared with conventional processes in order to avoid excessive solvent volumes. The carboxylic acid desirably has from 1 to 7 carbon atoms. In an embodiment, the carboxylic acid comprises acetic acid. The solvent may contain more than one carboxylic acid. For example, the solvent may further comprise benzoic acid. In another embodiment, the carboxylic acid of the solvent is acetic acid.

Optionally, an ionic solid, such as ammonium acetate ($NH_4OAc$) and/or ammonium bromide ($NH_4Br$), can be added to the mixture. Alternatively, a material which is capable of forming an ionic salt in solution can be added. The material can form the ionic salt in solution by combining with ions present in the solution. For example, in a solution containing bromide (for example in the form of HBr) or acetate ions (for example, in the form of acetic acid), ammonia could combine with the bromide or acetate ions forming ammonium bromide or ammonium acetate. The use of one or more ionic solids or materials capable of forming an ionic salt in solution provided an additional reduction in the level of impurities.

In an embodiment, the amount of ionic solid and material capable of forming an ionic salt in solution ranges from about 5 wt % to about 45 wt %, relative to the weight of the solvent, or from about 10 wt % to about 45 wt %, relative to the weight of the solvent. The solvent includes the carboxylic acid, the ionic liquid and/or ionic liquid precursors, the optional ionic solid or material capable of forming an ionic salt in solution, the optional water.

Optionally, the solvent may further comprise water. The water may be added to the mixture or generated in the mixture during the oxidation process. In an embodiment, the amount of water ranges from about 0.01 wt % to about 5 wt %, relative to the weight of the carboxylic acid. The amount of water may range from about 0.1 wt % to about 2 wt %, relative to the weight of the carboxylic acid.

In an embodiment, the ratio of solvent to p-xylene stream ranges from about 1:1 to about 10:1 by weight, or from about 1.5:1 to about 6:1 by weight, or from about 2:1 to about 4:1 by weight. The solvent includes the carboxylic acid, the ionic liquid and/or ionic liquid precursor, the optional ionic solid or material capable of forming an ionic salt in solution, the optional water.

The catalyst comprises at least one of cobalt, manganese, titanium, chromium, copper, nickel, vanadium, iron, molybdenum, tin, cerium and zirconium. In an embodiment, the catalyst comprises cobalt and manganese. The metal may be in the form of an inorganic or organic salt. For example, the metal catalyst may be in the form of a carboxylic acid salt, such as, a metal acetate and hydrates thereof. Exemplary catalysts include cobalt (II) acetate tetrahydrate and manganese (II) acetate, individually or in combination. In an embodiment, the amount of manganese (II) acetate is less than the amount of cobalt (II) acetate tetrahydrate by weight.

The amount of catalyst used in the invention may vary widely. For example, the amount of cobalt may range from about 0.001 wt % to about 2 wt % relative to the weight of the solvent. In an embodiment, the amount of cobalt ranges from about 0.05 wt % to about 2 wt % relative to the weight of the solvent. The amount of manganese may range from about 0.001 wt % to about 2 wt % relative to the weight of the solvent. In an embodiment, the amount of manganese ranges from about 0.05 wt % to about 2 wt % relative to the weight of the solvent. In another embodiment, the ratio of cobalt to manganese ranges from about 3:1 to about 1:2 by weight on an elemental metal basis.

Bromine sources are generally recognized in the art as being catalyst promoters and include bromine, ionic bromine, e.g. HBr, NaBr, KBr, $NH_4Br$; and/or organic bromides which are known to provide bromide ions at the oxidation conditions, such as, benzylbromide, mono and di-bromoacetic acid, bromoacetyl bromide, tetrabromoethane, ethylene dibromide. In an embodiment, the bromine source comprises or consists essentially of or consists of hydrogen bromide. The amount of hydrogen bromide may range from about 0.01 wt % to about 5 wt %, relative to the weight of the solvent. In another embodiment, the amount of hydrogen bromide ranges from about 0.05 wt % to about 2 wt %, relative to the weight of the solvent. The solvent includes the carboxylic acid, the ionic liquid and/or the ionic liquid precursors, the optional ionic solid or material capable of forming an ionic salt in solution, the optional water.

Suitable oxidizing agents for the process provide a source of oxygen atoms to oxidize the p-xylene and/or p-toluic acid, and/or another intermediate oxidization product at the oxidation conditions employed. Examples of oxidizing agents include peroxides, superoxides, and nitrogen compounds containing oxygen such as nitric acids. In an embodiment, the oxidizing agent is a gas comprising oxygen, e.g. air, carbon dioxide, and molecular oxygen. The gas may be a mixture of gasses. The amount of oxygen used in the process is preferably in excess of the stoichiometric amount required for the desired oxidation process. In an embodiment, the amount of oxygen contacted with the mixture ranges from about 1.2 times the stoichiometric amount to about 100 times the stoichiometric amount. Optionally, the amount of oxygen contacted with the mixture may range from about 2 times the stoichiometric amount to about 30 times the stoichiometric amount.

At least a portion of the components provides a liquid phase, although dissolution of one or more of the mixture components may not be complete at any or some time during the process. The liquid phase may be formed by mixing the components at ambient conditions. In another embodiment, the liquid phase is formed as the temperature of the mixture increases to the oxidation temperature. A mixture of the components may be formed prior to the oxidation step, in the same or different vessel as that used in the oxidation step. In another embodiment, a mixture of the components is formed in an oxidation reactor, e.g. adding various streams of the components individually and/or in combination to a continuous or semi-continuous oxidation reactor. The combined components, and/or various streams of the components may be heated before they are mixed together.

Though many conventional alkyl aromatic oxidation processes are typically conducted in a mixed phase, and often include three phases (e.g. solid, gas, and liquid), they are frequently referred to in the art as "liquid phase" oxidation processes because the oxidation conditions are maintained to provide at least a portion of the mixture in the liquid phase. It is also known in the art that the number of phases present may vary over time during the process. Processes according to the instant invention may also be conducted in a liquid phase or mixed phase in a similar manner as known in the art.

Conventional, liquid phase oxidation reactors as known in the art may be used to practice the invention. Examples include vessels, which may have one or more mechanical agitators, and various bubble column reactors such as those described in U.S. Pat. No. 7,692,036. It is also known to design, operate, and control such reactors and the oxidation reaction for the oxidation conditions employed including, e.g., the temperature, pressure, liquid and gas volumes, and corrosive nature of the liquid and gas phases where applicable. See, e.g. U.S. Pat. No. 7,692,036 and U.S. Pat. No. 6,137,001.

The contacting step[s] can take place under oxidizing conditions, if desired. Suitable oxidizing conditions generally include a temperature ranging from about 125° C. to about 275° C. and a pressure ranging from about atmospheric, i.e. 0 MPa(g), to about 6 MPa(g) and a residence time ranging from about 5 seconds to about 2 weeks. That is, the mixture has a temperature and a pressure within these ranges and may be maintained within these ranges for a period of time within the residence time range. In another embodiment, the temperature ranges from about 175° C. to about 225° C.; and the temperature may range from about 190° C. to about 235° C. In an embodiment, the pressure ranges from about 1.2 MPa(g) to about 6.0 MPa(g); and the pressure may range from about 1.5 MPa(g) to about 6.0 MPa(g). In a further embodiment, the residence time ranges from about 10 minutes to about 12 hours. The oxidation temperature, pressure and residence time may vary based on a variety of factors including for example, the reactor configuration, size, and whether the process is, batch, continuous, or semi-continuous. An oxidation condition may also vary based on other oxidation conditions. For example, use of a particular temperature range may enable use of a different residence time range.

In an embodiment, the terephthalic acid produced by the instant invention may precipitate, crystallize, or solidify in a liquid phase mixture at the oxidation conditions and/or as the mixture cools. Thus, a mixture according to the invention may further comprise solid terephthalic acid. Other compounds, including color bodies, and other oxidation products may solidify with or be trapped in the solid oxidation product thus reducing the purity of the desired product. In an embodiment, the mixture comprises a liquid phase. The mixture may comprise a gas phase such as when the oxidizing agent is added as a gas. The mixture may comprise a solid phase e.g. a mixture component, an oxidation product, or a by-product fails to dissolve or solidifies in the mixture. In an embodiment, the mixture comprises a liquid phase, a solid phase and optionally a gas phase. In another embodiment, the mixture comprises a liquid phase and a gas phase.

As noted above and discussed below, it has been discovered that the invention may be used to produce an oxidation product having different amounts of contaminants relative to those observed in conventional processes. In addition, the invention provides new ways to control the level of various contaminants in the oxidation product. In an embodiment, a process according to the invention further comprises forming the oxidation product as a solid, optionally at the oxidizing conditions, to produce the solid oxidation product and a mother liquor. The solid oxidation product may be separated from the mother liquor, i.e. liquid phase, and the mother liquor of the process may be recycled and reused in the contacting step or other steps of the process described below.

Processes according to the invention, may comprise one or more additional oxidizing steps. In an embodiment, a second oxidation step includes a second oxidizing temperature that is lower than the temperature of the first oxidizing step. Processes according to the invention may include additional contacting steps of the invention as described herein, and/or the invention may be combined with other oxidizing steps such as conventional oxidizing steps known in the art. Multiple contacting and/or oxidation steps may be conducted in series and/or parallel and may be combined with other process steps such as purification steps described herein.

In another embodiment, the invention further comprises purifying the oxidation product. Purifying may comprise one or more additional steps to isolate and purify the oxidation product. Examples of purifying steps include: separating wherein the oxidation product is separated from the mother liquor or another liquid phase such as by filtration and/or centrifugation; washing wherein the oxidation product is washed, for example with water and/or another solvent component; drying the oxidation product; and hydrogenation processes. Although hydrogenation processes can be used for purification, they are less desirable than other purification methods due to the cost. Such additional processing steps have been described in the general literature and are well known to those of ordinary skill in the art to be used in various combinations to purify oxidation products of the invention. See for example, the references cited in this application and the art cited therein.

A purification step of the instant invention may further comprise one or more solvent contacting steps. A solvent contacting step comprises contacting an oxidation product, also including washed or dried solid oxidation products, with a third solvent comprising at least one of water, a carboxylic acid, an ionic liquid and/or ionic liquid precursor, and a mother liquor to produce a purified oxidation product. In an embodiment, the solvent of the solvent contacting step contains ionic liquid and carboxylic acid, and optionally mother liquor. The composition of the solvent for the solvent contacting step can be as described above for the contacting step.

Solvent contacting may leach impurities from the solid oxidation product, and/or the oxidation product may be partially or completely dissolved in the solvent. Solvent contacting conditions include a solvent contacting temperature. The solvent contacting temperature may be lower than the oxidation temperature. In an embodiment, the solvent contacting temperature is at least 20° C. lower than the oxidation temperature. Solvent contacting may be practiced for example in the one or more crystallizers that follow the oxidation reactor in some conventional processes. The oxidation product may solidify, precipitate, or crystallize in the solvent of the solvent contacting step.

It should be noted that the terms "first", "second", and "third" etc. are being used to distinguish one component, or composition, or stage, or zone, or reactor etc. from another. It is not necessarily the case that a "second" stage or zone, for example, physically or temporally follows a "first" stage or zone. Depending on the context, it could be before or after, as would be understood by those of skill in the art.

EXAMPLES

The examples are presented to further illustrate some aspects and benefits of the invention and are not to be considered as limiting the scope of the invention.

Example 1

Experimental procedure: In a fume hood, load a Parr reactor with the specified amounts of components for the given experiment seal the reactor. The Parr reactor includes a gas distributor to disperse the gas through a 1.6 mm opening into the liquid, a mechanical gas entrainment stirrer, and baffles to ensure thorough mixing. Install the Parr reactor in a heater assembly at room temperature and connect a gas supply line to the reactor and a condenser to the reactor outlet. During operation, gases exit the reactor through the condenser then a trap, then a back-pressure regulator. Connect a safety vent having a rupture disk, and thermocouples to the reactor. Connect a cooling water recirculator to the condenser and begin to recirculate cooling water. Pressure test the Parr reactor at room temperature and 1.4 MPa(g) (200 psig) using nitrogen until there is no decrease in pressure for 15 minutes. Set the back pressure regulator on the reactor outlet to the experimental pressure and pressure test the reactor under nitrogen.

Begin raising the reactor temperature to the experimental temperature under the nitrogen atmosphere. Always follow all instructions for the specific reactor including temperature and pressure limits. When the reactor reaches the desired temperature begin adding air at the experimental rate and monitor the reactor temperature and pressure for the duration of the test. During the test, the air flow into the reactor is maintained at 1250 or 2500 standard $cm^3$ per minute, the pressure is maintained at 4.1 MPa(g), and the stirrer is maintained at 1600 rpm. At the end of the test shut off the heater, cut the air flow and allow the reactor to cool. When the reactor cools to less than about 35° C., open the back pressure valve, stop the cooling water, and remove and empty the reactor to obtain the solid oxidation product and mother liquor.

The mother liquor and products are filtered under vacuum to separate the solids and liquid. The solids are then mixed with approximately 100 cc deionized water at room temperature and decanted. The room temperature deionized water mixing and decanting is repeated two additional times. A fourth wash with deionized water is heated to approximately 95° C. for 30 minutes and then filtered. The solids are dried at 80° C. for 8-24 hours before analyzing.

Examples 2-9

Examples 2-9 were individual tests conducted using the equipment and procedure given in Example 1. The components of the mixture, given in grams, operating temperature, time, and air flow, and results are given in Table 1.

Example 2 (Comparative)

Conventional test run without ionic liquids to demonstrate the level of impurities made using conventional solvents under standard oxidizing conditions.

Example 3

Same oxidizing conditions as Example 2 except ionic liquids were substituted for some of the acetic acid. Incorporating ionic liquids significantly reduces the 4-CBA impurity, but causes higher levels of p-toluic acid and benzoic acid.

Example 4

Repeat of Example 3 except the oxidizing temperature was increased from 200 to 215° C. Increasing the temperature significantly reduced the 4-CBA and p-toluic acid content compared to Example 3, but caused an increase in benzoic acid.

Example 5

Same oxidizing conditions as Example 3. 1-butyl-3-methylimidazolium acetate was not used and the amounts of acetic acid, ammonium acetate and 1-butyl-3-methylimidazolium bromide were increased. Here, both the 4-CBA and p-toluic acid are significantly reduced compared to the conventional test (Example 2). The benzoic acid level is still higher than Example 2, but lower than Example 3.

Example 6

Repeat of Example 3 except the oxidation time was reduced to 6 hours, which resulted in higher 4-CBA and p-toluic acid impurities, and less benzoic acid.

Example 7

Repeat of Example 6 except ammonium acetate was not used. Using ammonium acetate significantly reduces the 4-CBA but results in higher p-toluic acid.

Example 8

Modified mixture components, increase air flow to 2500 standard cm³ per minute, increased oxidation temperature to 215° C. and decreased oxidation time to 3 hours. Changes significantly reduce the 4-CBA.

Example 9

Repeat of Example 8 except tetrabutylphosphonium bromide was used instead of 1-butyl-3-methylimidazolium bromide, and 1-butyl-3-methylimidazolium acetate and ammonium acetate were not used.

TABLE 1

| Example Number | 2 | 3 | 4 | 5 | 6 | 7 | 8 | 9 |
|---|---|---|---|---|---|---|---|---|
| Oxidation Temperature, ° C. | 200 | 200 | 215 | 200 | 200 | 200 | 215 | 215 |
| Oxidation Time, hours | 10 | 10 | 10 | 10 | 6 | 6 | 3 | 3 |
| Air Flow, standard cm3 per minute | 1250 | 1250 | 1250 | 1250 | 1250 | 1250 | 2500 | 2500 |
| Components (g) | | | | | | | | |
| p-Xylene | 20.0 | 20.0 | 20.0 | 20.0 | 20.0 | 20.0 | 20.0 | 20.0 |
| Acetic Acid | 100.0 | 44.0 | 44.0 | 60.0 | 44.0 | 44.0 | 50.0 | 80.0 |
| $H_2O$ | 2 | 0.4 | 0.4 | 0.4 | 0.4 | 0.4 | 0.4 | 0.4 |
| BMImOAc | 0 | 20.0 | 20.0 | 0 | 20.0 | 20.0 | 10.0 | 0 |
| BMImBr | 0 | 16.0 | 16.0 | 20.0 | 16.0 | 16.0 | 20.0 | 0 |
| tetrabutylphosphonium bromide | 0 | 0 | 0 | 0 | 0 | 0 | 0 | 20.0 |
| $NH_4OAc$ | 0 | 12.0 | 12.0 | 20.0 | 12.0 | 0.0 | 20.0 | 0 |
| HBr | 0.4 | 0.4 | 0.4 | 0.4 | 0.4 | 0.4 | 0.4 | 0.4 |
| $Co(OAc)_2$—$4H_2O$ | 0.8 | 0.8 | 0.8 | 0.8 | 0.8 | 0.8 | 0.8 | 0.8 |
| $Mn(OAc)_2$ | 0.6 | 0.6 | 0.6 | 0.6 | 0.6 | 0.6 | 0.6 | 0.6 |
| Analysis of Product | | | | | | | | |
| terephthalic acid, wt % | 98.5 | 97.8 | 98.9 | 99.9 | 96.4 | 97.0 | 99.9 | 98.4 |
| para-toluic acid, ppm-wt | 2,340 | 19,600 | 620 | 412 | 33,364 | 13,964 | 727 | 1,753 |
| 4-CBA (ppm) | 12,493 | 424 | 87 | 316 | 1,480 | 15,476 | 76 | 13,418 |
| Benzoic acid (ppm) | 167 | 1,742 | 5,001 | 421 | 532 | 430 | 640 | 79 |
| 4-hydoxymethyl-benzoic acid (ppm) | 403 | 678 | 0 | 0 | 989 | 496 | 0 | 253 |

Example 10

Experimental procedure: In a fume hood, load a Parr reactor with the specified amounts of components for the given experiment and seal the reactor. The Parr reactor includes a gas distributor to disperse the gas through a 1.6 mm opening into the liquid, a mechanical gas entrainment stirrer, and baffles to ensure thorough mixing. Install the Parr reactor in a heater assembly at room temperature and connect a gas supply line to the reactor and a condenser to the reactor outlet. During operation, gases exit the reactor through the condenser then a trap, then a back-pressure regulator. Connect a safety vent having a rupture disk, and thermocouples to the reactor. Connect a cooling water recirculator to the condenser and begin to recirculate cooling water. Pressure test the Parr reactor at room temperature and 1.4 MPa (g) (200 psig) using nitrogen until there is no decrease in pressure for 15 minutes. Set the back pressure regulator on the reactor outlet to the experimental pressure and pressure test the reactor under nitrogen.

Begin raising the reactor temperature to the experimental temperature under the nitrogen atmosphere. When the reactor reaches the desired temperature, begin adding air at the experimental rate and monitor the reactor temperature and pressure for the duration of the test. During the test, the air flow into the reactor is maintained at 1250 or 2500 standard cm³ per minute, the pressure is maintained at 4.1 MPa (g), and the stirrer is maintained at 1600 rpm.

For fast cool, at the end of the test shut off the heater, cut the air flow, and allow the reactor to cool. When the reactor cools to less than about 35° C., open the back pressure valve, stop the cooling water, and remove and empty the reactor to obtain the solid oxidation product and mother liquor.

For slow controlled cool down, the air was shut off, and the stirring was reduced to 350 rpm. The temperature was reduced by 15-20° C. and held for two hrs. Six temperature reductions were used between 215° C. and 100° C.

For hot filtering, slow cool the reactor to about 100° C. over 1 hr, depressurize and filter immediately the hot mixture to separate solids and solvents. Mix the solids in 60° C.-80° C. glacial acetic acid and filter, repeat once. Mix the solids in 60° C.-80° C. water and filter. Re-mix solids in water, heat to about 90° C. and stir for about 30 min., filter and dry at 80° C.

The mother liquor and products are filtered under vacuum to separate the solids and liquid. The solids are then mixed with approximately 100 cc deionized water at room temperature and decanted. The room temperature deionized water mixing and decanting is repeated two additional times. A fourth wash with deionized water is heated to approximately 95° C. for 30 minutes and then filtered. The solids are dried at 80° C. for 8-24 hours before analyzing.

The samples were visually rated from yellow to white, with white being more desirable.

CIELAB measurements were made on a Minolta CR300 series color meter using two light sources: Illuminant D65 and Illuminant C. D65 is a light standard defined by the CIE and is part of the D series of illuminants used to portray ambient illumination conditions around the world. D65 has a correlated color temperature (CCT) of 6504 K. Illuminant C is another representation of average day light with a CCT of 6774 K. The CIELAB measurements followed a procedure similar to that described in UOP SINCO Method 009 (Determination of Reflectance Color of Polyethylene Terephthalate (PET) Granules).

Examples 11-18

Examples 11-18 were individual tests conducted using the equipment and procedure given in Example 10. The components of the mixture, operating conditions, and results are given in Table 2.

Example 11 (Comparative)

Conventional test run without ionic liquids to demonstrate the level of impurities made using conventional solvents under standard oxidizing conditions.

Example 12

Same temperature as Example 11, but lower airflow and longer run time, and ionic liquids were substituted for some of the acetic acid. Incorporating ionic liquids significantly reduces the 4CBA impurity, but causes higher levels of p-toluic acid and benzoic acid. The b* was significantly reduced.

Example 13

Repeat of Example 12 except the oxidizing temperature was decreased from 215° C. to 200° C. and the run time was reduced. Decreasing the temperature significantly increased the 4-CBA and p-toluic acid content compared to Example 12, but caused a decrease in benzoic acid. The b* color value was slightly reduced.

Example 14

Same oxidizing conditions as Example 12 except the airflow was increased and the run time was decreased. Here, the 4-CBA is significantly reduced compared to the conventional test (Example 11), but is higher than Example 12. The p-toluic acid is significantly increased compared to the conventional test, and Example 12. The benzoic acid level is higher than Example 11, but lower than Example 12. The b* color value was slightly reduced compared to Example 12 and significantly reduced compared to the conventional test.

Example 15

Repeat of Example 14 except catalyst levels and bromine level were doubled, which significantly reduced 4-CBA, slightly decreased p-toluic acid, slightly increased benzoic acid, and the b* color value.

Example 16

Same oxidizing conditions, catalyst level, and bromine level as Example 14 except hot filtering was used, and acetic acid, 1-butyl-3-methylimidazolium bromide, and ammonium acetate were increased, and 1-butyl-3-methylimidazolium acetate was reduced. This significantly reduces the 4-CBA, p-toluic acid, and benzoic acid. The b* color value increased, and the visual color was off-white.

Example 17

Repeat of Example 16 except acetic acid was decreased and 1-butyl-3-methylimidazolium acetate was increased. The 4-CBA and p-toluic acid were significantly increased, and the benzoic acid was slightly decreased. The b* color value decreased.

Example 18

Repeat of Example 17 except 1-butyl-3-methylimidazolium acetate was decreased, and 1-butyl-3-methylimidazolium bromide, and ammonium acetate were increased. The 4-CBA was decreased, and p-toluic acid was significantly increased, and the benzoic acid was slightly increased. The b* color value slightly increased.

The b* values for the samples ranged from 2 to 6 (an average of measurements using Illuminates C and D65). The b* value for the baseline test made without ionic liquid was 26.4. Thus, the present invention represents a significant reduction in the b* value without the necessity of prior art purification processes.

Including ionic liquids in the composition makes whiter terephthalic acid products with significantly lower b* standard color numbers than those made without ionic liquid's.

TABLE 2

| Example number | 11 | 12 | 13 | 14 | 15 | 16 | 17 | 18 |
|---|---|---|---|---|---|---|---|---|
| Oxidation Temperature, ° C. | 215 | 215 | 200 | 215 | 215 | 215 | 215 | 215 |
| Oxidation Time, hrs | 3 | 10 | 6 | 3 | 3 | 3 | 3 | 3 |
| Air Flow, sccm | 2500 | 1250 | 1250 | 2500 | 2500 | 2500 | 2500 | 2500 |
| Cooling | Fast | Slow controlled | Slow controlled | Fast | Fast | Hot Filtering | Fast | Fast |

TABLE 2-continued

| Example number | 11 | 12 | 13 | 14 | 15 | 16 | 17 | 18 |
|---|---|---|---|---|---|---|---|---|
| Components (g) | | | | | | | | |
| p-Xylene | 20 | 20 | 20 | 20 | 20 | 20 | 20 | 20 |
| Acetic Acid | 100 | 44 | 44 | 44 | 44 | 50 | 45 | 45 |
| BMImOAc | 0 | 20 | 20 | 20 | 20 | 10 | 15 | 11 |
| BMImBr | 0 | 16 | 16 | 16 | 16 | 20 | 20 | 22 |
| $NH_4OAc$ | 0 | 12 | 12 | 12 | 12 | 20 | 20 | 22 |
| HBr | 0.4 | 0.4 | 0.4 | 0.4 | 0.8 | 0.4 | 0.4 | 0.4 |
| $H_2O$ | 2 | 0.4 | 0.4 | 0.4 | 0.4 | 0.4 | 0.4 | 0.4 |
| $Co(OAc)_2$—$4H_2O$ | 0.8 | 0.8 | 0.8 | 0.8 | 1.6 | 0.8 | 0.8 | 0.8 |
| $Mn(OAc)_2$ | 0.6 | 0.6 | 0.6 | 0.6 | 1.2 | 0.6 | 0.6 | 0.6 |
| Analysis of Product | | | | | | | | |
| 4-CBA (ppm) | 7707 | 62 | 626 | 1081 | 239 | 76 | 696 | 489 |
| Benzoic acid (ppm) | 182 | 1644 | 330 | 1163 | 1243 | 640 | 601 | 710 |
| p-Toluic acid (ppm) | 1379 | 12040 | 19423 | 25607 | 23881 | 727 | 38149 | 17482 |
| Visual Product Color | Yellow | White | White | White | White | Off-white | White | White |
| Color Analysis, L* value | 78.8 | 95.2 | 93.3 | 91.8 | 93.2 | 94.2 | 93.8 | 94.5 |
| Color Analysis, a* value | 1.4 | −1.7 | −1.4 | −1.8 | −1.8 | −1.2 | −1.7 | −1.7 |
| Color Analysis, b* value | 26.4 | 3.8 | 2.2 | 2.9 | 3.9 | 5.9 | 3.8 | 3.9 |

Example 19

Additional tests were run to analyze the effect of the amounts of acetic acid, 1-butyl-3-methylimidazolium acetate, 1-butyl-3-methylimidazolium bromide, and ammonium acetate on the level of various impurities. The p-xylene to solvent ratios were held constant in the tests. The tests were run using the procedure described above. The oxidation conditions were 215° C., 4.1 MPa, with 2500 sccm airflow for 3 hr. The component levels are shown in Table 2.

TABLE 3

| Components (g) | 1 | 2 | 3 | 4 | 5 |
|---|---|---|---|---|---|
| Acetic Acid | 45 | 50 | 60 | 80 | 100 |
| BMImBr | 20 | 20 | 20 | 20 | 0 |
| $NH_4OAc$ | 20 | 20 | 20 | 0 | 0 |
| BMImOAc | 15 | 10 | 0 | 0 | 0 |

Figure 1:
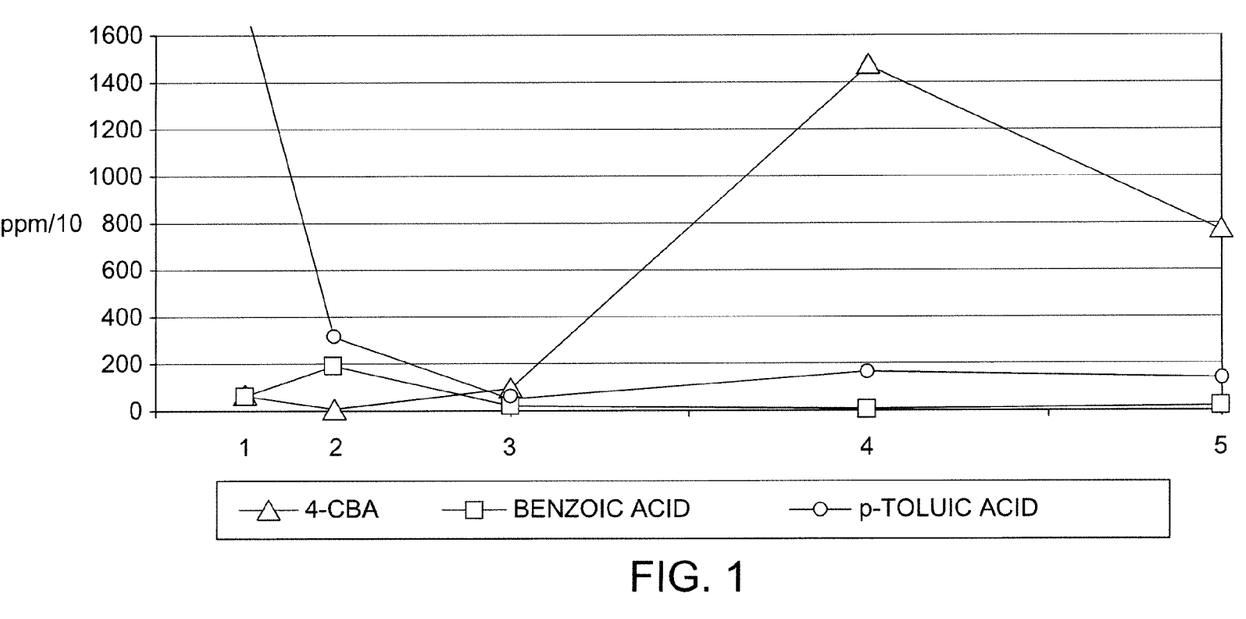
FIG. 1 is graph showing the impurity level of various solvent compositions.

The results are shown in FIG. 1. The lowest level of 4-CBA, 46 ppm, was for composition 2.

Example 20

Figure 2:
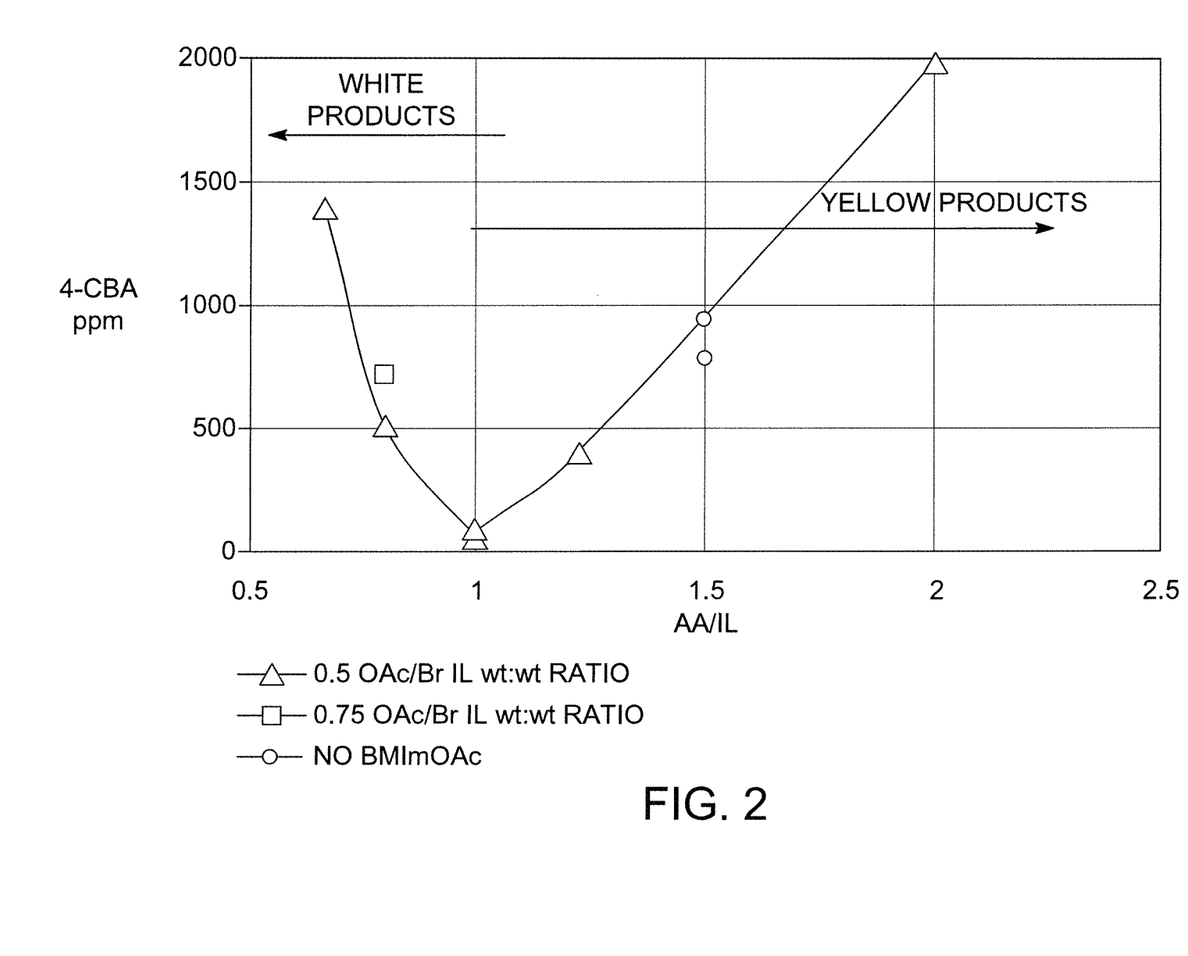
FIG. 2 is a graph showing the level of 4-CBA as a function of the ratio of carboxylic acid to ionic liquid.

Additional tests were run to analyze the effect of the ratio of acetic acid to ionic liquid (the combination of 1-butyl-3-methylimidazolium acetate, 1-butyl-3-methylimidazolium bromide, and ammonium acetate) and the ratio of 1-butyl-3-methylimidazolium acetate to 1-butyl-3-methylimidazolium bromide on color and level of 4-CBA. The tests were run using the procedure described above. The oxidation conditions were 215° C., 4.1 MPa, with 2500 sccm airflow for 3 hr. The ratio of 1-butyl-3-methylimidazolium bromide to ammonium acetate was maintained at 1:1. The results are shown in FIG. 2.

The ratio of acetic acid to ionic liquid is desirably about 1:1, and the ratio of 1-butyl-3-methylimidazolium acetate to 1-butyl-3-methylimidazolium bromide is desirably about 0.5 to obtain the whitest products with the lowest level of 4-CBA.

Thus, a desirable blend of ionic liquid has a AA:BMImBr:NH$_4$OAc:BMImOAc weight ratio of about 5:2:2:1 produces the lowest level of 4-CBA and an acceptable white color.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

What is claimed is:

1. A process for oxidizing an alkyl-aromatic compound comprising:
    contacting an alkyl-aromatic compound, a solvent, a bromine source, a catalyst, and
    an oxidizing agent to produce a product comprising terephthalic acid and wherein a CIELAB b* value of the terephthalic acid is less than about 5;
    wherein the solvent comprises a carboxylic acid and an ionic liquid and wherein the solvent has a ratio of the carboxylic acid to the ionic liquid within a range of about 7:13 and 13:7 by weight; and
    wherein a cation of the ionic liquid is selected from the group consisting of imidazoles, pyrazoles, thiazoles, isothiazoles, azathiazoles, oxothiazoles, oxazolines, oxazaboroles, dithiazoles, triazoles, selenozoles, oxaphospholes, pyrroles, boroles, furans, thiophenes, phospholes, pentazoles, indoles, indulines, oxazoles, isothiazoles, tetrazoles, benzofuran, dibenzofurans, benzothiophenes, dibenzpthiophenes, thiadiazoles, pyrdines, pyrimidines, pyrazines, pyridazines, piperazines, piperidines, morpholines, pyrans, anilines, phthalazines, quinazolines, quinoxaline, and combinations thereof.

2. The process of claim 1, wherein the product contains less than about 2500 ppm of 4-carboxybenzaldehyde.

3. The process of claim 1,
    wherein an anion of the ionic liquid is selected from the group consisting of halides, borides, phosphates, arsenates, stibates, acetate, carboxylates, azolates, sulfates, acyl units, $CO_3^{2-}$; $NO_2^{1-}$, $NO_3^{1-}$, $SO_4^{2-}$, $PO_4^{3-}$, $(CF_3)SO_3^{1-}$ and combinations thereof.

4. The process of claim 1, wherein the contacting step further comprises adding an ionic solid or a material capable of forming an ionic salt.

5. The process of claim 1, wherein the ionic liquid comprises 1-butyl 3-methyl imidazolium bromide and 1-butyl 3-methyl imidazolium acetate.

6. The process of claim 5, wherein a ratio of 1-butyl 3-methyl imidazolium bromide to 1-butyl 3-methyl imidazolium acetate is about 1:3 to 3:1.

7. The process of claim 5, wherein the mixture further comprises ammonium acetate, and wherein a ratio of carboxylic acid to 1-butyl 3-methyl imidazolium bromide to ammonium acetate to 1-butyl 3-methyl imidazolium acetate is about 10:1:1:1 to 1:5:5:5.

8. The process of claim 1, wherein the ionic liquid is formed in situ from at least one ionic liquid precursor.

9. A process for oxidizing an alkyl-aromatic compound comprising:
contacting an alkyl-aromatic compound, a solvent, a bromine source, a catalyst, and
an oxidizing agent to produce a product comprising terephthalic acid and wherein a CIELAB b* value of the terephthalic acid is less than about 5; and
maintaining a 4-CBA level in the product of less than about 2500 ppm by controlling a ratio of the solvent.

10. The process of claim 9, wherein the solvent comprises a carboxylic acid and an ionic liquid, and wherein the 4-CBA level is maintained by controlling the ratio of the carboxylic acid to the ionic liquid within a range of about 7:13 to 13:7.

11. The process of claim 9, wherein the ionic liquid comprises 1-butyl 3-methyl imidazolium bromide and 1-butyl 3-methyl imidazolium acetate, wherein the mixture further comprises ammonium acetate, and wherein a ratio of carboxylic acid to 1-butyl 3-methyl imidazolium bromide to ammonium acetate to 1-butyl 3-methyl imidazolium acetate is about 10:1:1:1 to 1:5:5:5.

12. The process of claim 9, further comprising purifying the product.

13. A process for oxidizing an alkyl-aromatic compound comprising:
contacting an alkyl-aromatic compound, a solvent, a bromine source, a catalyst, and
an oxidizing agent to produce a product comprising at least one of an aromatic alcohol, an aromatic aldehyde, an aromatic ketone, and an aromatic carboxylic acid; and
maintaining a CIELAB b* value of the product to less than about 5 by controlling a ratio of the solvent.

14. The process of claim 13, wherein the solvent comprises a carboxylic acid and an ionic liquid, and wherein the CIELAB b* value is maintained by controlling the ratio of the carboxylic acid to the ionic liquid within a range of about 7:13 to 13:7.

15. The process of claim 13, wherein the oxidation product contains less than about 2500 ppm of 4-carboxybenzaldehyde.

16. The process of claim 13, wherein the ionic liquid comprises 1-butyl 3-methyl imidazolium bromide and 1-butyl 3-methyl imidazolium acetate, wherein the mixture further comprises ammonium acetate, and wherein a ratio of carboxylic acid to 1-butyl 3-methyl imidazolium bromide to ammonium acetate to 1- butyl 3-methyl imidazolium acetate is about 10:1:1:1 to 1:5:5:5.

17. The process of claim 9 wherein the contacting step further comprises adding an ionic solid or a material capable of forming an ionic salt.

18. The process of claim 13, wherein the contacting step further comprises adding an ionic solid or a material capable of forming an ionic salt.

19. The process of claim 9, wherein the ionic liquid is formed in situ from at least one ionic liquid precursor.

20. The process of claim 13, wherein the ionic liquid is formed in situ from at least one ionic liquid precursor.

* * * * *

UNITED STATES PATENT AND TRADEMARK OFFICE
CERTIFICATE OF CORRECTION

Page 1 of 1

PATENT NO. : 8,946,471 B2
APPLICATION NO. : 13/340152
DATED : February 3, 2015
INVENTOR(S) : Bhattacharyya et al.

It is certified that error appears in the above-identified patent and that said Letters Patent is hereby corrected as shown below:

Title Page, Item (75) Inventors, should read

-- (75) Inventors: Alakananda Bhattacharyya, Des Plaines, IL (US); Joel T. Walenga, Des Plaines, IL (US); Raymond Shih, Elgin, IL (US) --.

Signed and Sealed this
Fifteenth Day of March, 2016

Michelle K. Lee
*Director of the United States Patent and Trademark Office*